United States Patent [19]

Shu

[11] Patent Number: 5,286,365
[45] Date of Patent: Feb. 15, 1994

[54] GRAPHITE-BASED SOLID STATE POLYMERIC MEMBRANE ION-SELECTIVE ELECTRODES

[75] Inventor: Frank R. Shu, La Habra Heights, Calif.

[73] Assignee: Beckman Instruments, Inc., Fullerton, Calif.

[21] Appl. No.: 821,158

[22] Filed: Jan. 15, 1992

[51] Int. Cl.$^5$ .......................................... G01N 27/414
[52] U.S. Cl. .................................... 204/418; 204/416
[58] Field of Search ............................ 204/416–419

[56] References Cited

U.S. PATENT DOCUMENTS

| | | | |
|---|---|---|---|
| 3,314,864 | 4/1967 | Hersch | 204/431 |
| 3,662,745 | 5/1972 | Cosentino | 204/435 |
| 3,856,649 | 12/1974 | Genshaw et al. | 204/418 |
| 3,957,607 | 5/1976 | Simon et al. | 204/418 |
| 4,115,209 | 9/1978 | Freiser et al. | 204/418 |
| 4,271,002 | 6/1981 | Hawkins | 204/418 |
| 4,276,141 | 6/1981 | Hawkins | 204/418 |
| 4,303,408 | 12/1981 | Kim | 204/418 |
| 4,431,508 | 2/1984 | Brown, Jr. et al. | 204/418 |
| 4,454,007 | 6/1984 | Pace | 204/416 |
| 4,504,368 | 3/1985 | Delton et al. | 204/418 |
| 4,528,085 | 7/1985 | Kitajima et al. | 204/416 |
| 4,549,951 | 10/1985 | Knudson et al. | 204/416 |
| 4,649,218 | 3/1987 | Shanzer et al. | 564/197 |
| 4,683,048 | 7/1987 | Yamada et al. | 204/416 |
| 4,859,306 | 8/1989 | Siddiqi et al. | 204/418 |
| 5,078,856 | 1/1992 | Yamaguchi et al. | 204/418 |

FOREIGN PATENT DOCUMENTS

| | | |
|---|---|---|
| 0174572A2 | of 0000 | European Pat. Off. |
| 0262582 | 4/1988 | European Pat. Off. |
| 920499 | 4/1983 | U.S.S.R. |
| 935776 | 6/1983 | U.S.S.R. |

OTHER PUBLICATIONS

*Handbook of Chemistry and Physics*, 55th Ed., 1974–1975, p. D-121.

K. Hiiro et al., "Perchlorate-Selective Electrodes with Urushi as the Membrane Matrix", *Anal. Chim. Acta*, 110:321 (1979).

E. Metzger et al., "Ion Selective Liquid Membrane Electrode for the Assay of Lithium in Blood Serum", *Anal. Chem.*, 58:132–135 (1986).

E. Metzger et al., "Lithium/Sodium Ion Concentration Ratio Measurements in Blood Serum with Lithum and Sodium Ion Selective Liquid Membrane Electrodes", *Anal. Chem.*, 59:1600–1603 (1987).

V. P. Y. Gadzekpo et al., "Problems in the Application of Ion-Selective Electrodes in Serum Lithium Analysis", *Analyst*, 111:567–570 (1986).

K. Kimura et al., "Lithium Ion Selective Electrodes Based on Crown Ethers for Serum Lithium Assay", *Anal. Chem.*, 59:2331–2334 (1987).

*Primary Examiner*—T. Tung
*Attorney, Agent, or Firm*—William H. May; Gary T. Hampson; Michael B. Farber

[57] ABSTRACT

An improved solid-state ion-selective electrode has greater uniformity of asymmetric potential and high sensitivity and selectivity for the cation of interest. The electrode comprises: (1) a porous element comprising graphite; (2) an electrochemical reference in substantially dry form on at least a portion of the element, the reference comprising: (a) an oxidant and (b) a reductant that is the conjugate of the oxidant, the oxidant and reductant being present in about equimolar quantities; and (3) a polymeric membrane comprising an ion-selective ionophore in electrochemical contact with the electrochemical reference. The electrode can be prepared to be selective for one of a number of cations, including lithium and ammonium. Methods for preparing these electrodes are also disclosed.

15 Claims, 1 Drawing Sheet

AMMONIUM ELECTRODE
(GRAPHITE-BASED INTERNAL REFERENCE)

GRAPHITE-BASED SOLID STATE POLYMERIC MEMBRANE ION-SELECTIVE ELECTRODES

BACKGROUND

For many clinical and research purposes, it is necessary to measure the concentration of ions, particularly cations such as lithium, ammonium, sodium, potassium, or calcium, in biological fluids such as serum, plasma, or urine.

In recent years, physiological electrolyte analyzers based on ion-selective electrode (ISE) technology have been used increasingly in the clinical laboratory and doctor's office for the determination of such ions as $H^+$, $Na^+$, $K^+$, and $Ca^{2+}$. These analyzers are as simple and as rapid to use as the familiar pH meter. In such analyzers, an ISE is used together with an external reference electrode in such a manner that they are simultaneously immersed in a sample solution. An electrical potential is developed between the electrodes which is related to the presence of the ion to which the ISE is sensitive. The potential is proportional to the logarithm of the ion concentration. The relationship between potential and the logarithm of the ion concentration is described by the Nernst equation. The intercept of the potential on the y-axis, i.e., the potential at an infinitesimal ion concentration, is referred to as the offset.

The traditional methods for monitoring lithium ion concentrations, however, have been atomic absorption spectroscopy and flame emission photometry. Although accurate and precise, these methods are time-consuming, require very expensive and cumbersome equipment, and are not particularly suited to automation. The time and expense required make such methods unsuitable for rapid monitoring of serum lithium concentration in a doctor's office, as should be done with patients receiving lithium.

Likewise, ammonia ion concentration has been measured by conductimetry and by the reaction with phenol in the presence of hypochlorite to form a chromogen, indophenol. These methods for ammonium measurement are not ideal as they are time-consuming and require complex equipment and several reagents.

Although the measurement of lithium and ammonia using ISE technology would be an improvement over these prior measurement techniques, the use of ISE technology has presented several challenges. For example, an ISE useful for lithium determination must meet several rigorous criteria. Most importantly, such an ISE must be highly selective for lithium over other cations found in serum, particularly sodium and potassium. The level of $NA^+$ in serum is typically over 1400 times the lowest lithium levels of clinical importance. The ISE for lithium should also have good sensitivity so that concentrations of lithium in serum of about 0.2 mmol/L can be accurately determined, and, for the most accurate measurement, a plot of electrode potential against the logarithm of lithium concentration should be linear or nearly so in the concentration region of interest. The ISE must also be resistant to interference from organic molecules found in blood serum, especially lipoproteins and other proteins. Rapid and stable response to lithium ion is also highly desirable. Resistance to water hydration when exposed to aqueous samples is also extremely important when providing a lithium ISE useful commercially. The occurrence of hydration requires that electrodes be changed at intervals of only a few weeks or even days. This has proven to be a great obstacle to a commercially useable lithium ISE.

ISEs have been developed by T. Shono, using crown ethers as lithium-selective ionophores (K. Kimura et al., *Anal. Chem.* 59:2331–2334 (1987)), and by Dr. W. Simon in Zurich, using ionophores known as "neutral ligands" (EPO Publication No. 017452 A2; E. Metzger, *Anal. Chem.* 58:132–135 (1986); E. Metzger, *Anal. Chem.* 59:1600–1603 (1987)). While these publications demonstrate the principal that lithium-selective and neutral ligand ionophores are useful, the ISEs described are not suitable for clinical applications due to limited performance characteristics.

As part of the measurement circuit of an ISE, an internal reference electrode is required. In traditional prior ISEs, this was usually made with a silver/silver chloride electrode in contact with a liquid reference solution that was in turn in contact with the ion-selective membrane. In more recent designs, the liquid internal reference electrode has been replaced by a solid support in the form of an electrical element or substrate (U.S. Pat. No. 4,276,141 to Hawkins; U.S. Pat. No. 3,856,649 to Genshaw et al.). However, a primary cause for problems with known solid support ISEs is believed to be related to difficulties attributed to the physical adhesion between the ion selective layer and the electrical element or substrate. Such an element or substrate can be a wire or a semiconductor (ISEFET). Another form of such an element or substrate is a silver-silver chloride pellet made by pressurizing a silver and silver chloride powder mix at very high pressure. With each of these types of elements or substrates, however, there is believed to be insufficient porosity to retain the ion-selective layer or membrane in sufficiently good physical contact to insure good electrochemical interaction.

Even more recently, a polymeric membrane ISE design using graphite as the internal reference electrode has been described (U.S. Pat. No. 4,549,951 to Knudson et al.; U.S. Pat. No. 4,431,508 to Brown et al.). Of these two approaches, only Brown et al. describes pre-treating the graphite substrate to help stabilize drift, but even Brown et al. is unsatisfactory for routine clinical analysis because the offset, i.e., the intercept of the Nernst equation E°, varies from electrode to electrode in a broad range. This is undesirable because the offset, sometimes referred to as the asymmetric potential (AP), must match with the instrument on which the electrode is to be used, and mismatches can lead to analytical error.

Therefore, there is a need for an improved design of ISEs, particularly for the detection of lithium and ammonium, but also for detection of other cations such as sodium and potassium. Such ISEs should be selective and sensitive and respond rapidly. They should be resistant to interference from serum components such as proteins and lipids. They should provide for improved electrochemical interaction between the electrically conductive element and the sample through a polymeric ion selective layer. Most importantly, they should have a very narrow offset or AP range to improve matching of the electrode with the instrument with which it is to be used.

SUMMARY

New ion-selective electrodes in accordance with the present invention meet these needs. These electrodes are sensitive and selective and have a very narrow range of asymmetric potential, thus improving analytical accuracy.

Most generally, a solid-state cation-selective electrode according to the present invention comprises:

(1) a porous element comprising graphite;

(2) an electrochemical reference in substantially dry form on at least a portion of the element, the reference comprising a redox buffer which is composed of: (a) an oxidant and (b) a reductant that is the conjugate of the oxidant, the oxidant and reductant being present in about equimolar quantities; and (3) a polymeric membrane comprising an ion-selective ionophore in contact with the electrochemical reference.

Preferably, the electrochemical reference is selected from the group consisting of ferricyanide/ferrocyanide, iodide/triiodide, iodide/polyvinylpyrrolidone-iodine complex, ferrocene/ferricinium derivatives, and reduced and oxidized form of iron or copper complexes of aromatic ligands rich in $\pi$-electrons. More preferably, the electrochemical reference is selected from the group consisting of ferricyanide/ferrocyanide and iodide/triiodide.

The electrochemical reference can further comprise a concentration of pH buffer sufficient to stabilize the electrode against the effect of $CO_2$ in a physiological sample containing $CO_2$ in equilibrium with atmospheric $CO_2$. Alternatively, or in addition, the electrochemical reference can further comprise a concentration of the cation for which the ion-selective ionophore is selective sufficient to increase the sensitivity of the electrode when the electrode is used to measure the cation in a physiological sample.

The electrode can be prepared to be selective for one of a number of ions. Typically, the electrode is selective for a cation, more typically, $Li^+$ or $NH_4^+$.

When the electrode is selective for $Li^+$, the cation-selective ionophore included in the polymeric membrane is preferably selected from a group consisting of crown ethers, crown ether derivatives, and mixtures thereof. Most preferably, the $Li^+$-selective ionophore is 6,6-dibenzyl-14-crown-4 ether.

When the ion-selective electrode is selective for $NH_4^+$, the cation-selective ionophore is preferably selected from the group consisting of nonactin, monactin, and mixtures thereof. Most preferably, the cation-selective ionophore is nonactin.

Preferably, the polymeric membrane comprises, in addition to the ion-selective ionophore:

(a) a lipophilic-hydrophilic polymer adhesive to the electrochemical reference having an intrinsic viscosity of from about 1 to about 1.5 ml/g; and (b) a plasticizer.

Preferably, the adhesive lipophilic-hydrophilic polymer having an intrinsic viscosity of from about 1 to about 1.5 ml/g is a polyvinyl chloride polymer.

Alternatively, the polymeric membrane can comprise a polymer selected from the group consisting of silicone rubber, polyacrylate polymers, cellulose acetate, ethyl cellulose, collodion, polyurethane, and Urushi lacquer.

A particular electrode according to the present invention suitable for measurement of $Li^+$ comprises:

(1) a porous graphite rod;

(2) an electrochemical reference produced by drying a solution of a reductant and its conjugate oxidant on the rod, the concentration of the reductant and the oxidant in the solution being from about 0.001 M/L to about 0.1 M/L each, the reductant and oxidant preferably being selected from the group consisting of ferricyanide/ferrocyanide and iodide/triiodide; and (3) a polyvinyl chloride membrane containing 6,6-dibenzyl-14-crown-4 ether in contact with the electrochemical reference.

Another particular electrode according to the present invention suitable for measurement of $NH_4^+$ comprises:

(1) a porous graphite rod;

(2) an electrochemical reference produced by drying a solution of a oxidant and its conjugate reductant on the rod, the concentration of the oxidant and the reductant in the solution being from about 0.001 M/L to about 0.1 M/L each, the reductant and oxidant preferably being selected from the group consisting of ferricyanide/ferrocyanide and iodide/triiodide; and (3) a polyvinyl chloride membrane containing: (a) nonactin and (b) diisodecyl adipate both in contact with the electrochemical reference.

Another aspect of the present invention is a process of making the ion-selective electrodes described above. The process comprises:

(1) providing a porous element comprising graphite to serve as support for an electrode;

(2) exposing a surface of the porous element;

(3) forming an electrochemical reference on the exposed surface, including applying a redox buffer solution to the surface of the porous element exposed in step (2), the solution comprising solutes including at least: (a) an oxidant and (b) a reductant that is the conjugate of the reductant, the oxidant and reductant being present in about equimolar quantities in the solution;

(4) drying the solution on the surface such that the solutes are in contact with the element; and (5) applying a polymeric membrane containing an ion-selective ionophore to the element on which the redox buffer solution has dried such that the polymeric membrane is in electrochemical contact with the solutes.

BRIEF DESCRIPTION OF THE DRAWINGS

These and other features, aspects, and advantages of the present invention will become better understood with reference to the following description, appended claims, and accompanying drawings where:

DESCRIPTION

An improved solid-state ion-selective electrode (ISE) is particularly useful for quantitation of lithium and ammonium, as well as other cations. This electrode is sensitive, selective, and has an asymmetric potential within a narrow range, improving its suitability for analytical use.

Figure 1:
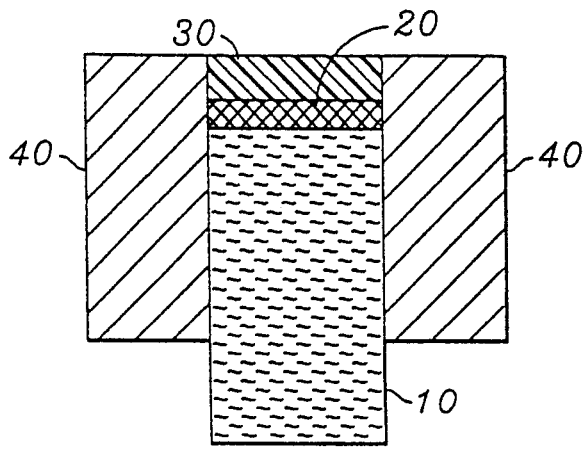
FIG. 1 is a diagram of a solid-state cation-selective electrode of the present invention.

With reference to FIG. 1, the electrode comprises:

(1) a porous element 10 comprising graphite;

(2) an electrochemical reference 20 comprising a redox buffer which is composed of: (a) an oxidant and (b) a reductant that is the conjugate of the reductant, the oxidant and reductant being present in about equimolar quantities, the electrochemical reference 20 in substantially dry form on at least a portion of the element 10; and (3) a polymeric membrane 30 comprising an ion-selective ionophore in electrochemical contact with the electrochemical reference 20.

The electrode can be placed in a polyvinyl chloride housing 40 for protection and convenience of use.

The electrode constitutes an electrochemical cell whose voltage varies linearly with the logarithm of the ion for which the ion-selective ionophore is selective. The voltage can be measured against an external reference electrode, such as a calomel electrode with, for example, a high input impedance digital voltmeter connected between the porous element 10 and the external reference electrode.

I. THE ELECTRODE

A. The Porous Element

The porous element comprising graphite is preferably a porous graphite rod. The graphite rod is of a suitable length and diameter for insertion into a sample of from about 0.1 ml to about 10 ml. Typically, the rod is about 5 mm in diameter. The length of the rod is not critical and can be from about 6 mm to at least 15 cm long; typically, it is from about 6 mm to about 40 mm. A preferred graphite rod is POCO model AXZ-5Q1, an ultra-fine grade (POCO Graphite, Inc., Decatur, Tex.) but any porous graphite rod free from contaminants can be used.

B. The Electrochemical Reference

The electrochemical reference comprises a redox buffer which is composed of: (a) an oxidant and (b) a reductant that is the conjugate of the oxidant. The term "conjugate" is used herein to describe pairs of reactants of which one member of the pair can be converted into the other member by means of an oxidation-reduction reaction. The oxidant and reductant are present in about equimolar quantities. The electrochemical reference is coated in substantially dry form on at least a portion of the element and is typically applied to the element from a solution that is then allowed to dry. The solution can be an aqueous solution or an aqueous solution containing up to about 75% methanol.

The oxidant and reductant can be ferricyanide/ferrocyanide, iodide/triiodide, iodide/polyvinylpyrrolidone-iodine complex, ferrocene/ferricinium derivatives, or reduced and oxidized forms of iron or copper complexes of aromatic ligands rich in $\pi$-electrons such as derivatives of 1,1-phenanthroline, bipyridine, and sulfonated phthalocyanines. Preferably, the oxidant-reductant is ferricyanide/ferrocyanide or iodide/triiodide. Prussian Blue is the reaction product of ferricyanide with ferrocyanide and can be applied to the porous graphite element as a simple electrochemical reference.

Preferably, the concentration of the oxidant and reductant in the solution from which the oxidant and reductant are applied to the element is from about 0.001 M/L to about 0.1 M. For the ferricyanide/ferrocyanide couple, the preferred concentration is about 0.04 M. For the iodide/triiodide couple, the preferred concentration is about 0.01 M/L of triiodide with 0.005 M/L of iodine in excess in a solution containing 75% methanol.

The presence in the electrochemical reference of a low concentration of the ion of interest may benefit the performance of the electrode, e.g., lithium chloride for the lithium electrode, by increasing the sensitivity of the electrode. The concentration of the ion of interest is typically from about 0.1 mmol/L to about 10 mmol/L, preferably about 1 mmol/L.

Because graphite is sensitive to pH, the incorporation of a low concentration of pH buffer in the electrochemical reference may also be desirable to reduce the effect of $CO_2$ in some applications, such as in the case of direct potentiometric measurements of electrolytes in blood. The concentration of pH buffer used is sufficient to stabilize the electrode against the effect of $CO_2$ in a physiological sample in equilibrium with atmospheric $CO_2$. Preferably, the pH buffer is phosphate buffer, pH 7, and its concentration is from about 2 mmol/L to about 50 mmol/L, more preferably about 10 mmol/L.

C. The Polymeric Membrane Containing the Ion-Selective Ionophore

1. The Membrane Components

The polymeric membrane preferably comprises in addition to the ion-selective ionophore:

(1) a lipophilic-hydrophilic polymer adhesive to the electrochemical reference and having an intrinsic viscosity of from about 1 to 1.5 ml/g; and (2) a plasticizer.

Preferably, the adhesive lipophilic-hydrophilic polymer is a polyvinyl chloride polymer.

Plasticizers for use in ion-selective membranes are well-known in the art; a number of suitable plasticizers are described in U.S. Pat. No. 4,276,141 to Hawkins, incorporated herein by this reference. For lithium-selective membranes, a preferred plasticizer is fluoronitrodiphenyl ether together with trioctyl phosphate; another preferred plasticizer is nitrophenyloctyl ether together with trioctyl phosphate. The membrane can also contain potassium tetrakis (p-chlorophenyl)borate.

Where the ISE is selective for ammonium ion, a preferred plasticizer is diisodecyl adipate.

In a less preferred alternative, the polyvinyl matrix is replaced by another polymer, such as, but not limited to, silicone rubber, a polyacrylate polymer, cellulose acetate, ethyl cellulose, collodion, polyurethane, or Urushi lacquer (K. Hiiro et al., *Anal. Chim. Acta* 110:321 (1979)).

2. The Ion-Selective Ionophore

The ion-selective ionophore is chosen according to the ion intended to be measured. When the ionophore is chosen to be selective for $Li^+$ the ionophore is preferably selected from the group of crown ethers, crown ether derivatives, and mixtures thereof. More preferably, the ionophore is 6,6-dibenzyl-14-crown-4 ether.

When the ionophore is chosen to be selective for $NH_4^+$ the ionophore is preferably selected from the group consisting of nonactin and monactin. Most preferably, the ionophore is nonactin.

Other ion-selective ionophores are well-known in the art for other cations such as sodium, potassium, and calcium. For potassium, the ion-selective ionophore is preferably gramicidin, valinomycin, dimethyldibenzo-30-crown-10 ether, or dibenzo-18-crown-6 ether. For calcium, suitable ion-selective ionophores are described in U.S. Pat. No. 4,271,002 by Hawkins, incorporated herein in its entirety by this reference.

3. Proportions of Ingredients

A preferred formula for the polymeric membrane for a lithium-selective electrode is:

| | |
|---|---|
| 6,6-dibenzyl-14-crown-4 ether | 1.8% |
| FNDPE (fluoronitrodiphenyl ether) | 50.9% |

-continued

| | |
|---|---|
| potassium tetrakis(p-chlorophenyl)borate | 0.9% |
| polyvinyl chloride | 41.8% |
| trioctyl phosphate | 4.6% |

Another preferred formula for the polymeric membrane for a lithium-selective electrode is:

| | |
|---|---|
| 6,6-dibenzyl-14-crown-4 ether | 2.0% |
| NPOE (nitrophenyloctyl ether) | 53.2% |
| potassium tetrakis(p-chlorophenyl)borate | 1.0% |
| polyvinyl chloride | 41.6% |
| trioctyl phoshate | 2.2% |

A preferred formula for the polymeric membrane for an ammonium-selective electrode is:

| | |
|---|---|
| nonactin | 1.1% |
| polyvinyl chloride | 29.7% |
| DIDA (diisodecyl adipate) | 69.2% |

II. MANUFACTURE OF THE ELECTRODE

The process of manufacturing an electrode according to the present invention is as follows:

(1) providing a porous element comprising graphite to serve as support;

(2) exposing a surface of the porous element;

(3) forming an electrochemical reference on the exposed surface, including applying a redox buffer solution to the surface of the porous element exposed in step (2), the solution comprising solutes including at least: (i) an oxidant and (ii) a reductant that is the conjugate of the reductant, the oxidant and reductant being present in about equimolar quantities in the solution;

(4) drying the redox buffer solution on the surface such that the solutes are in contact with the element; and (5) applying a polymeric membrane containing an ion-selective ionophore to the element on which the redox buffer solution has dried such that the polymeric membrane is in electrochemical contact with the solutes; and, optionally, (6) placing the coated element into a housing of polyvinyl chloride (FIG. 1).

The exposing of a clean surface of the rod is preferably done by sanding, most preferably with a 600 grit sandpaper. Preferably, the surface of the graphite rod is then cleaned by rinsing with a solvent such as methanol. The electrochemical reference is typically applied to the graphite rod in a volume of about 15 to about 20 µl. Alternatively, the rod can be dipped into a solution of the electrochemical reference, typically for about 25 seconds. The electrochemical reference is preferably dried on the surface of the graphite rod in an oven at 45° C. overnight.

The polymeric membrane to be applied to the element, after application of the electrochemical reference, is preferably prepared by the following steps:

(a) mixing together the adhesive lipophilic-hydrophilic polymer and the plasticizer;

(b) adding a solvent such as cyclohexanone;

(c) mixing the polymer, the plasticizer, and the solvent thoroughly;

(d) optionally, heating to about 50° C. to promote thorough mixing;

(e) if the mixture was heated, cooling to room temperature; and (f) adding the ion-selective ionophore, which can be in solution with a solvent such as cyclohexanone.

The membrane is typically applied in two coats, with a 3- to 4-hour interval between the first and second coat. The volume of the membrane applied is typically about 25 microliters in each coat.

III. USE OF THE ION-SELECTIVE ELECTRODE

The ion-selective electrode is used to detect the ion of choice by placing the electrode in a potentiometric circuit and recording the potential generated with respect to an external reference electrode when the ion-selective electrode and external reference electrode are placed in the sample containing the ion, in much the same way as a pH meter is used. The sample is preferably diluted before use, typically about 20-fold. In some applications, it is desirable to deproteinize the sample, as proteins or lipoproteins may coat the electrode, interfering with the measurement.

The invention is illustrated by the following examples. The examples are for illustrative purposes and are not to be construed as limiting the scope of the invention in any manner.

EXAMPLES

Example I

Lithium Ion Electrode

Three lithium-selective electrodes were prepared as described above. In particular, 3 POCO model AXZ-5-Q graphite rods (15 cm length × 5 mm diameter), were sanded with 600 grit sandpaper and cleaned by rinsing with methanol. For two of these electrodes, a redox buffer comprised of ferricyanide and ferrocyanide was used for the electrochemical reference. Specifically, 20 microliters of a 0.04 M/L solution of ferricyanide/ferrocyanide was applied to the rod. The rods were then dried in an oven at 45° C. overnight. The third electrode, a control, was not treated with the ferricyanide-ferrocyanide redox buffer solution. A polymeric membrane of the following composition:

| | |
|---|---|
| 6,6-dibenzyl-14-crown-4 ether | 1.8% |
| FNDPE (fluoronitrodiphenyl ether) | 50.9% |
| potassium tetrakis(p-chlorophenyl)borate | 0.9% |
| polyvinyl chloride | 41.8% |
| trioctyl phosphate | 4.6% | was applied to the rods in two 25-µl coats, with an interval of 3 to 4 hours between the coats.

For the testing of these electrodes, Li standards ranging from 0.1 mmol/L to 2.0 mmol/L were used. Each Li standard contained 140 mmol/L of NaCl. Each sample was diluted 20-fold with an 0.3 M/L Tris-phosphate buffer containing 0.05 mmol/L of LiCl in the background.

The test results with lithium are summarized in Table I. The data of Table I clearly demonstrate the advantages of using a redox buffer to control the offset of the asymmetric potential of the electrode. In addition, the sensitivity and the selectivity of the lithium electrode was also improved by coating the graphite with redox buffer. The sodium selectivity for the electrodes employing the redox buffer is about two times better than that of corresponding electrodes with a silver-silver chloride internal reference electrode.

TABLE I

RESPONSE OF LITHIUM-SELECTIVE ELECTRODES

| Standard | Li, mmol/L | E, mv Electrode #1 | E, mv Electrode #2 | E, mv Electrode #3 |
|---|---|---|---|---|
| 1 | 0.1 | 176.8 | 176.3 | −44.0 |
| 2 | 0.5 | 183.8 | 184.0 | −35.0 |
| 3 | 1.0 | 190.1 | 191.8 | −27.8 |
| 4 | 1.5 | 194.7 | 197.4 | −23.3 |
| 5 | 2.0 | 199.6 | 202.2 | −21.5 |

Notes:
(1) Electrodes #1 and #2 were coated with the redox buffer; Electrode #3 was not.

Example II

Ammonium-Selective Electrode

An ammonium-selective electrode was made in the same manner as the lithium-selective electrode of Example I. The ferricyanide/ferrocyanide system was used as the electrochemical reference. The polymeric membrane was made with PVC, nonactin, and diisodecyl adipate in the following proportions:

| | |
|---|---|
| nonactin | 1.1% |
| polyvinyl chloride | 29.7% |
| DIDA (diisodecyl adipate) | 69.2%. |

Figure 2:
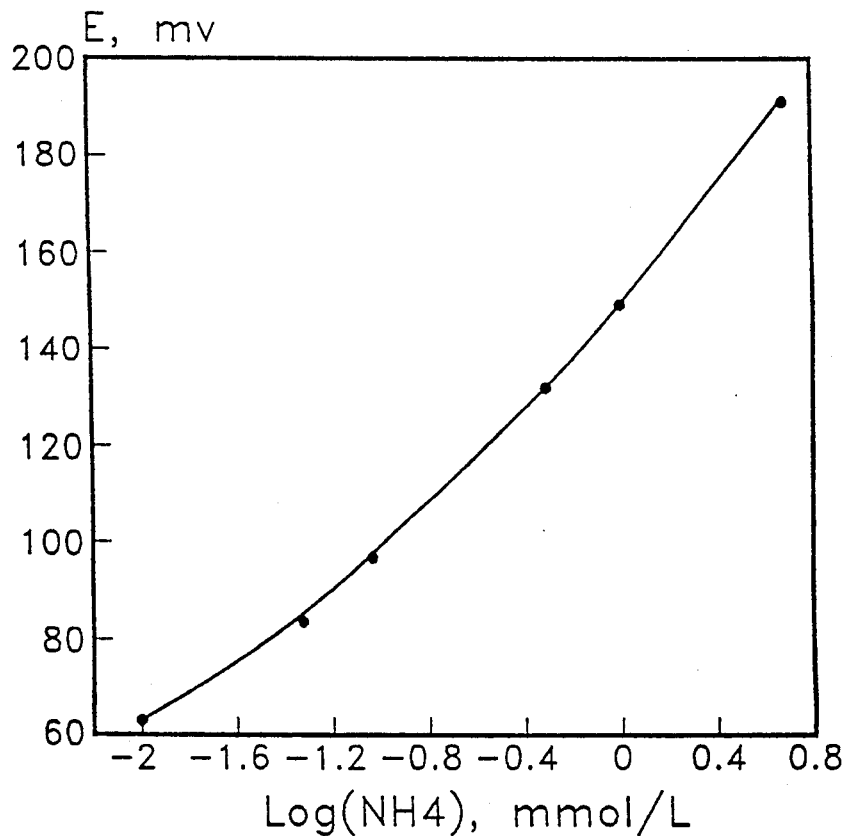
FIG. 2 is a plot of the voltage generated versus the logarithm of the ammonium concentration for an ammonium-selective electrode of the present invention.

The linearity and sensitivity of this electrode are illustrated in FIG. 2. These results show the suitability of the ammonium-selective electrode across for measurement of ammonium concentration across a broad concentration range.

ADVANTAGES OF THE INVENTION

The present invention provides ion-selective electrodes of improved sensitivity and selectivity. In particular, these electrodes have a stable and reproducible offset or asymmetric potential, improving the reliability of measurement of ion concentration. These electrodes are particularly suitable for measurement of lithium or ammonium, but can be used for measurement of other ions, particularly other cations, by use of the appropriate ion-selective ionophores.

Although the present invention has been described with considerable detail, with reference to certain preferred versions thereof, other versions are possible. Therefore, the spirit and scope of the appended claims should not be limited to the description of the preferred versions contained herein.

I claim:

1. A solid-state ion-selective electrode comprising:
   (a) a porous element comprising graphite;
   (b) an electrochemical reference in substantially dry form on at least a portion of the element, the reference comprising:
      (i) an oxidant;
      (ii) a reductant that is the conjugate of the oxidant, the oxidant and reductant being present in about equimolar quantities; and
      (iii) a concentration of the ion for which the ion-selective electrode is selective sufficient to increase the sensitivity of the electrode when the electrode is used to measure the ion in a physiological sample; and
   (c) a polymeric membrane comprising an ion-selective ionophore selective for the ion incorporated in the electrochemical reference in contact with the electrochemical reference.

2. The ion-selective electrode of claim 1 wherein the electrochemical reference is selected from the group consisting of ferricyanide/ferrocyanide, iodide/triiodide, iodide/polyvinylpyrrolidone-iodine complex, ferrocene/ferricinium derivatives, and reduced and oxidized forms of iron or copper complexes of aromatic ligands rich in $\pi$-electrons.

3. The ion-selective electrode of claim 1 wherein the electrochemical reference is ferricyanide/ferrocyanide.

4. The ion-selective electrode of claim 1 wherein the electrochemical reference is iodide/triiodide.

5. The ion-selective electrode of claim 1 wherein the ion-selective ionophore is selective for $Li^+$.

6. The ion-selective electrode of claim 5 wherein the ion-selective ionophore is selected from a group consisting of crown ethers, crown ether derivatives, and mixtures thereof.

7. The ion-selective electrode of claim 6 wherein the ion-selective ionophore is 6,6-dibenzyl-14-crown-4 ether.

8. The ion-selective electrode of claim 1 wherein the polymeric membrane comprises, in addition to the ion-selective ionophore:
   (i) a lipophilic-hydrophilic polymer adhesively attached to the electrochemical reference and having an intrinsic viscosity of from about 1 to about 1.5 ml/g; and
   (ii) a lipophilic-hydrophlic plasticizer.

9. The ion-selective electrode of claim 1 wherein the ion-selective ionophore is selective for $NH_4^+$.

10. The ion-selective electrode of claim 9 wherein the ion-selective ionophore is selected from the group consisting of nonactin, monactin, and mixtures thereof.

11. The ion-selective electrode of claim 10 wherein the ion-selective ionophore is nonactin.

12. The ion-selective electrode of claim 1 wherein the concentration of the ion for which the ion-selective ionophore is selective is from about 0.1 mM to about 10 mM in the electrochemical reference.

13. The ion-selective electrode of claim 1 wherein the polymeric membrane comprises a polymer selected from the group consisting of silicone rubber, polyacrylate polymers, cellulose acetate, ethyl cellulose, collodion, polyurethane, and Urushi lacquer.

14. A solid-state ammonium-selective electrode comprising:
   (a) a porous graphite rod;
   (b) an electrochemical reference comprising:
      (i) an equimolar quantity of a reductant and its conjugate oxidant in substantially dry form on the graphite rod, the reference produced by drying a solution of the oxidant and its conjugate reductant on the rod, the concentration of the oxidant and reductant in the solution being from about 0.001 M/L to about 0.1 M/L each, the reductant and oxidant being selected from the group consisting of ferricyanide/ferrocyanide and iodide/triiodide; and
      (ii) a concentration of ammonium ion from about 0.01 mM to about 10 mM; and
   (c) a polyvinyl chloride membrane containing: (i) nonactin and (ii) diisodecyl adipate both in contact with the electrochemical reference.

15. A solid-state lithium-selective electrode comprising:
   (a) a porous graphite rod;

(b) an electrochemical reference comprising an equimolar quantity of a reductant and its conjugate oxidant in substantially dry form on the graphite rod, the reference produced by drying of a solution of the reductant and its conjugate oxidant on the rod, the concentration of the reductant and the oxidant in the solution being from about 0.001 M/L to about 0.1 M/L each, the reductant and oxidant being selected from the group consisting of ferricyanide/ferrocyanide and iodide/triiodide and further comprising a concentration of lithium ion from about 0.1 mM to about 10 mM; and (c) a polyvinyl chloride membrane containing 6,6-dibenzyl-14-crown-4 ether in contact with the electrochemical reference.

* * * * *